(12) United States Patent
Gigi

(10) Patent No.: US 8,932,232 B2
(45) Date of Patent: Jan. 13, 2015

(54) TISSUE SAMPLING DEVICE AND METHOD

(75) Inventor: Igal Gigi, Givataim (IL)

(73) Assignee: Arch Medical Devices Ltd., Rishpon (IL)

( * ) Notice: Subject to any disclaimer, the term of this patent is extended or adjusted under 35 U.S.C. 154(b) by 524 days.

(21) Appl. No.: 13/260,570

(22) PCT Filed: Mar. 24, 2010

(86) PCT No.: PCT/IB2010/051289
§ 371 (c)(1),
(2), (4) Date: Sep. 27, 2011

(87) PCT Pub. No.: WO2010/113080
PCT Pub. Date: Oct. 7, 2010

(65) Prior Publication Data
US 2012/0022396 A1 Jan. 26, 2012

(30) Foreign Application Priority Data
Mar. 31, 2009 (GB) ................................ 0905512.0

(51) Int. Cl.
*A61B 10/00* (2006.01)
*A61B 10/04* (2006.01)
*A61B 10/02* (2006.01)
*A61B 17/32* (2006.01)

(52) U.S. Cl.
CPC ............. *A61B 10/04* (2013.01); *A61B 10/0275* (2013.01); *A61B 2010/045* (2013.01); *A61B 2017/320064* (2013.01)
USPC ............................................ 600/564; 604/22

(58) Field of Classification Search
CPC .................................................. A61B 10/0275
USPC ................................ 600/564; 604/22; 606/41
See application file for complete search history.

(56) References Cited

U.S. PATENT DOCUMENTS

| 2,822,808 A | 2/1958 | Boone et al. |
| 3,007,471 A | 11/1961 | McClure, Jr. |
| 3,289,669 A | 12/1966 | Dwyer et al. |

(Continued)

FOREIGN PATENT DOCUMENTS

| WO | WO 00/12008 | 3/2000 |
| WO | WO 2006/015302 | 2/2006 |
| WO | WO 2010/113080 | 10/2010 |

OTHER PUBLICATIONS

Communication Pursuant to Rules 70(2) and 70a(2) EPC Dated Jul. 12, 2013 From the European Patent Office Re. Application No. 10758131.6.

(Continued)

*Primary Examiner* — Max Hindenburg
*Assistant Examiner* — Renee Danega

(57) ABSTRACT

A device and method for collecting a tissue sample. The device includes a blade comprising an anterior portion and an elongated blade body. The elongated blade body is substantially firm and the anterior portion is bendable. The anterior portion comprises a sharp or pointed anterior end adapted to pierce and penetrate into tissue and a sampling mechanism with at least one recess or notch disposed therein or a sampling channel to collect the tissue sample. The sheath comprises an elongated body having an interior lumen, and an arcuate slot corresponding in shape to the blade and forming a continuum between the interior lumen and an exterior aperture laterally on the body of the sheath.

17 Claims, 7 Drawing Sheets

(56) References Cited

U.S. PATENT DOCUMENTS

| | | | |
|---|---|---|---|
| 3,844,272 A | 10/1974 | Banko | |
| 4,243,049 A | 1/1981 | Goodale et al. | |
| 4,724,840 A | 2/1988 | McVay et al. | |
| 4,989,614 A | 2/1991 | Dejter, Jr. et al. | |
| 5,301,684 A | 4/1994 | Ogirala | |
| 5,527,331 A | 6/1996 | Kresch et al. | |
| 5,527,340 A | 6/1996 | Vogel | |
| 6,228,039 B1 | 5/2001 | Binmoeller | |
| 6,632,182 B1 | 10/2003 | Treat | |
| 6,752,767 B2 | 6/2004 | Turovskiy et al. | |
| 6,936,014 B2 | 8/2005 | Vetter et al. | |
| 7,473,232 B2 | 1/2009 | Teague | |
| 2001/0001811 A1 | 5/2001 | Burney et al. | |
| 2001/0005778 A1 | 6/2001 | Ouchi | |
| 2002/0022788 A1 | 2/2002 | Corvi et al. | |
| 2002/0059938 A1* | 5/2002 | Fogarty et al. | 128/899 |
| 2002/0183758 A1 | 12/2002 | Middleton et al. | |
| 2004/0158143 A1* | 8/2004 | Flaherty et al. | 600/407 |
| 2004/0167433 A1* | 8/2004 | Fisher | 600/570 |
| 2007/0244353 A1* | 10/2007 | Larsen | 600/105 |
| 2008/0114364 A1* | 5/2008 | Goldin et al. | 606/79 |
| 2009/0036936 A1* | 2/2009 | Solsberg et al. | 606/86 R |
| 2010/0076303 A1 | 3/2010 | McKinley | |

OTHER PUBLICATIONS

Supplementary European Search Report and the European Search Opinion Dated Jun. 25, 2013 From the European Patent Office Re. Application No. 10758131.6.

International Preliminary Report on Patentability Dated Oct. 13, 2011 From the International Bureau of WIPO Re. Application No. PCT/IB 2010/051289.

International Search Report Dated Sep. 14, 2010 From the International Searching Authority Re. Application No. PCT/IB2010/051289.

Patents Act 1977: Combined Search and Examination Report Under Sections 17 and 18(3) Dated Jul. 27, 2009 From the Intellectual Property Office of the Untied Kingdom Re. Application No. GB0905512.0.

Patents Act 1977: Conflict With a Corresponding PCT Patent Application Dated May 10, 2011 From the Intellectual Property Office of the United Kingdom Re. Application No. GB0905512.0.

* cited by examiner

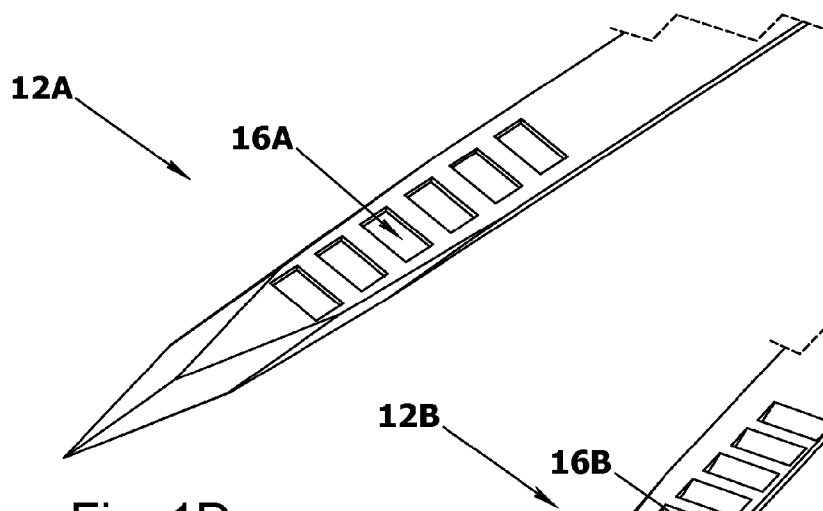
Fig. 1D
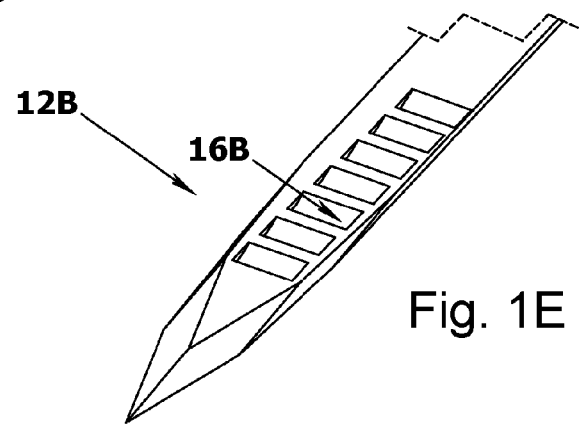
Fig. 1E
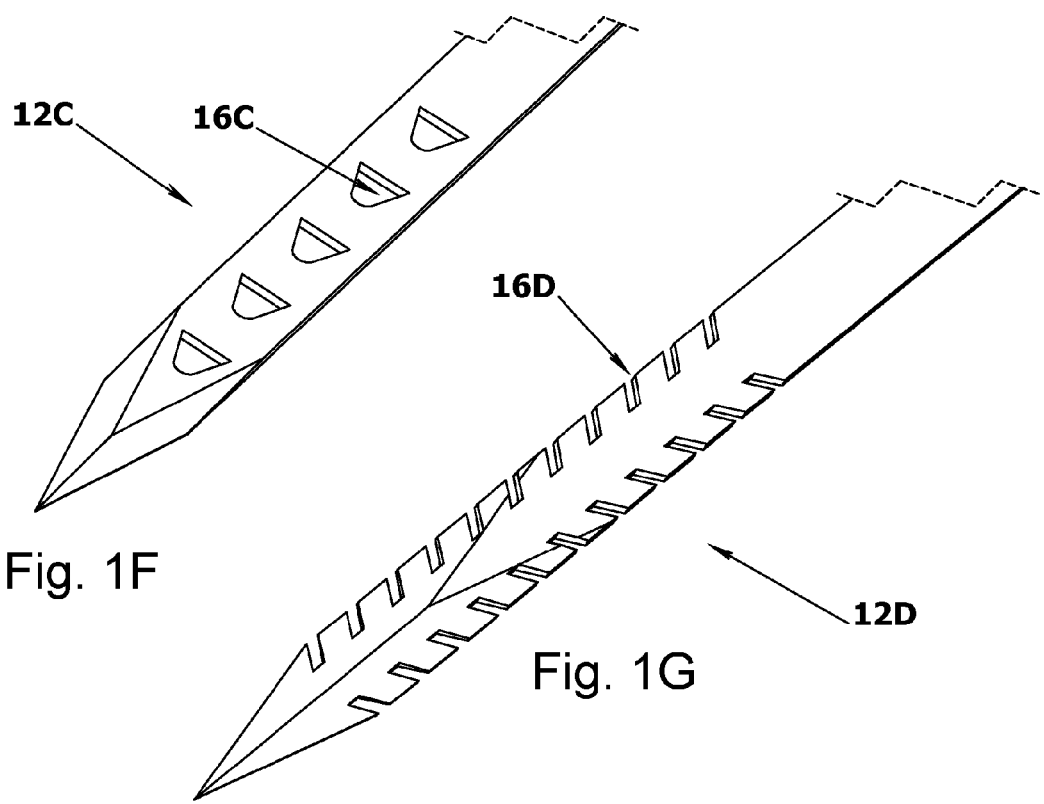
Fig. 1F
Fig. 1G

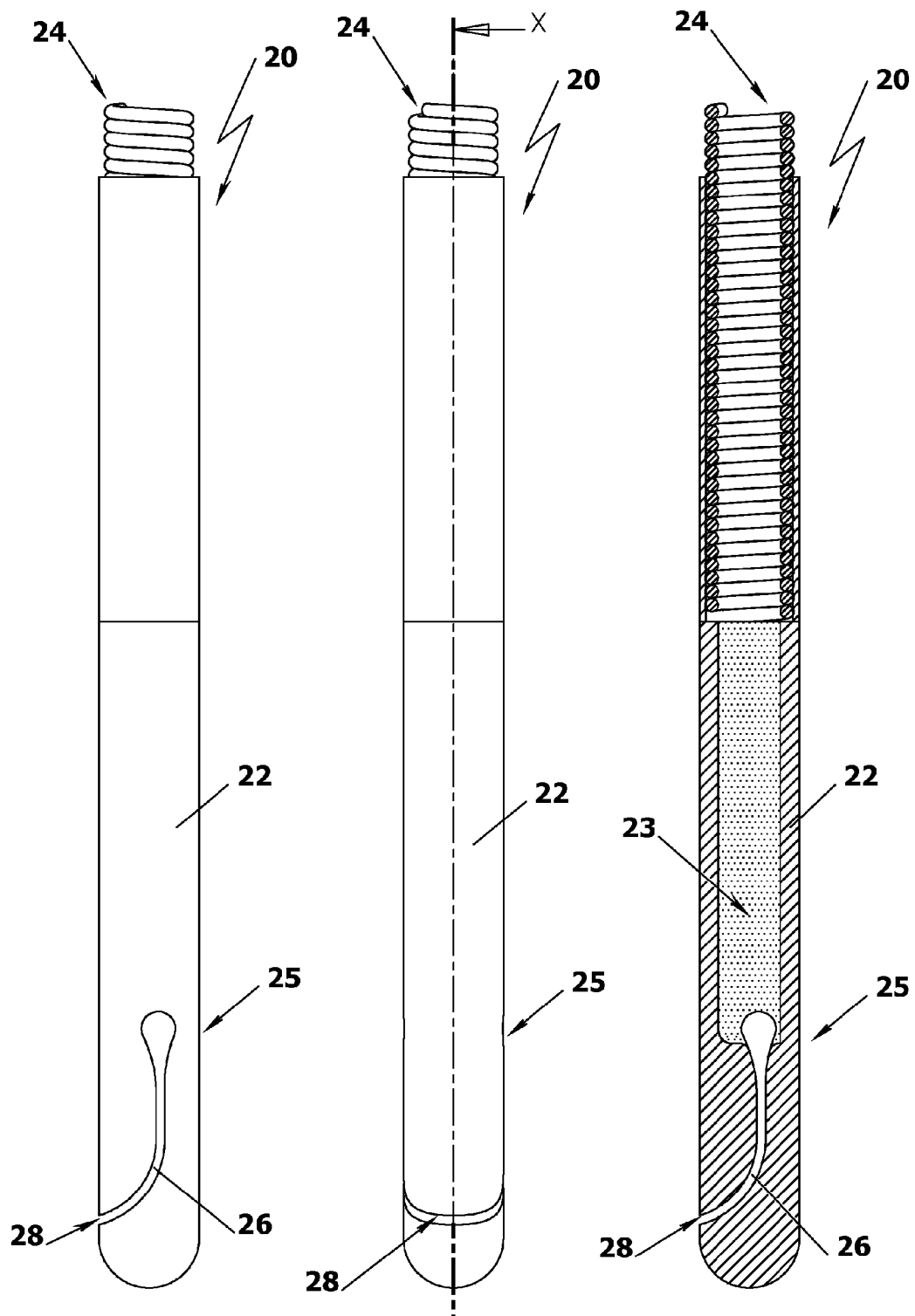

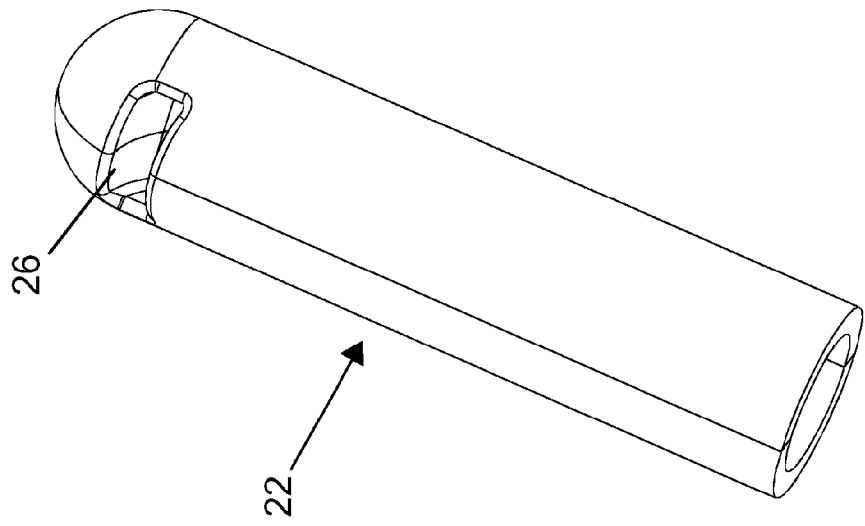
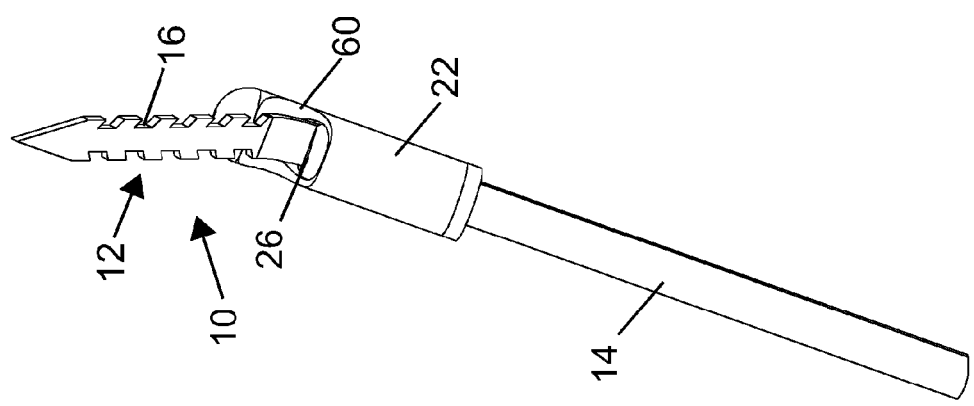
Fig. 5A
Fig. 5B

TISSUE SAMPLING DEVICE AND METHOD

RELATED APPLICATIONS

This application is a National Phase of PCT Patent Application No. PCT/IB2010/051289 having International filing date of Mar. 24, 2010, which claims the benefit of priority of U.K. Patent Application No. 0905512.0 filed on Mar. 31, 2009. The contents of the above applications are all incorporated herein by reference.

TECHNICAL FIELD

The present invention, in general, relates to a device and method for collecting tissue samples. More particularly, the present invention relates to a device that allows minimally invasive collection of tissue samples and a method of using the same.

BACKGROUND

Sampling of organ tissue or the like is often required to help in the diagnosis and disease staging of a patient. Numerous tools and devices for such purpose have been disclosed, which typically comprise a narrow elongated guide or sheath through which a sampling needle or blade is advanced to take a sample, and then retracted. The tools are commonly designed for taking a sample from tissue located axial to the tool, i.e. in front of (in continuation with) the end of the tool.

To allow taking a sample lateral to the sampling device, WO 2006/015,302 (Schomer/X-Sten) discloses a method for treating stenosis in a spine including inserting a tissue removal tool into tissue in the working zone. In some embodiments, the tissue removal tool has a side aperture from which a resilient tissue-engaging hook with a pre-configured in a curvilinear shape is retained within the tool by an outer cutting member. When the cutting member is retracted, the curved shape of the hook urges the hook's outer end to extend outward through the side aperture. This activity is particularly shown in FIGS. 10-14, especially FIG. 12 of the publication.

US 2002/183,758 (Middleton) discloses a tissue cavitation device which can be used to remove tissue, including lateral to the longitudinal axis of the device. A flexible cutting element is extendable from the distal end (away from the longitudinal axis) of a shaft/insertion tube of the device. The cutting element is spring loaded like a leaf spring so that upon distally exiting from the shaft/insertion tube, the cutting element lateral returns a bent or curved shape and thus extends both longitudinally and laterally from the distal end of the shaft. This feature is particularly well shown in FIGS. 2B and 4C.

The lateral sampling of the aforementioned publications, being based on spring loading (biasing) of the sampling element tends to result in a sweeping movement of the sampling element when the element exits the guide (sheath, shaft), which may cause undesirable collateral damage to the tissue. Further, such designs may require penetration of the guide itself into the tissue to be sampled and not merely the blade or other such sampling element. Moreover, the penetration strength of the sampling element/blade is mainly and perhaps merely a result of the biasing.

SUMMARY OF THE INVENTION

There are provided in accordance with some preferred embodiments of the present invention a device for collecting tissue samples and a method of using the same, as set forth in the claims hereunder. The tissue samples can be taken from a variety of body parts or organs including, but not limited to, lungs, pancreas, gastro-intestinal organs, urinary system, vascula, and so on.

According to embodiments of one aspect of the present invention there is provided a tissue sample collecting device as defined in claim 1 and its dependent claims, e.g. according to some embodiments, the tissue sample collecting device comprises: a blade comprising an anterior portion and an elongated blade body, the blade body being substantially firm and the anterior portion being substantially flat, bendable and comprising a sharp or pointed anterior end adapted to pierce and penetrate into tissue and having a sampling mechanism adapted to accommodate the tissue sample; and a sheath comprising an elongated sheath body having an interior lumen with an arcuate slot forming a continuum between the interior lumen and an exterior aperture at the end thereof, wherein the exterior aperture is disposed laterally (i.e. not longitudinally) on the sheath body and the cross section of the arcuate slot generally corresponds in shape to the longitudinal profile of the blade.

The term "sheath" or "applicator" or derivatives thereof, shall be used to denote any appropriate guide or guiding device for the tissue sampling element (hereinafter in the specification and claims, "blade" or derivative thereof).

According to embodiments of another aspect of the present invention there is provided a method of operating a tissue sample collecting device as defined in claim 17 its dependent claims, e.g. according to some embodiments, a method of operating the device for collecting a tissue sample comprising: providing a tissue sampling device comprising: a blade with an anterior portion and an elongated blade body, the anterior portion comprising a sampling mechanism adapted to accommodate the tissue sample; and a sheath comprising an elongated sheath body having an interior lumen with an arcuate slot forming a continuum between the interior lumen and an exterior aperture at the end thereof, the exterior aperture disposed laterally on the sheath body and the cross section of the arcuate slot generally corresponding in shape to the longitudinal profile of the blade; positioning the sheath so that the exterior aperture of the arcuate slot faces the tissue to be sampled; inserting the blade into the sheath until the anterior portion protrudes linearly from the exterior aperture, and into the tissue to be sampled; and extracting a tissue sample.

BRIEF DESCRIPTION OF THE DRAWINGS

The invention may be understood upon reading of the following detailed description of non-limiting exemplary embodiments thereof, with reference to the following drawings, in which:

FIGS. 1D-1G are plan views illustrating exemplary anterior portions of the blade;

FIGS. 3A-3C are respective side, front and cross-sectional side views of an exemplary guide in the form of an sheath body or sheath of an embodiment of the tissue sampling device of the present application;

FIGS. 5A and 5B are a perspective view of other embodiments of the present tissue sampling device illustrating exemplary sheath body/sheath designs.

The following detailed description of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DISCLOSURE OF EMBODIMENTS OF THE INVENTION

Illustrative embodiments of the invention are described below. In the interest of clarity, not all features of an actual implementation are described in this specification. In this regard, such devices are often used in conjunction with an endoscope or bronchoscope (e.g. reside within the endoscope), but which for clarity are not shown, though understood by a person in the art. Likewise, typically the movement of the device and sampling blade thereof is commonly controlled by a specially designed handle—also not shown. It will be appreciated that in the development of any such actual embodiment, numerous implementation-specific decisions must be made to achieve the developers' specific goals, such as compliance with system-related and business-related constraints, which vary from one implementation to another. Moreover, it will be appreciated that such a development effort might be complex and time-consuming, but would nevertheless be a routine undertaking for those of ordinary skill in the art having the benefit of this disclosure.

Sample Collecting Device of the Invention

Figure 1A:
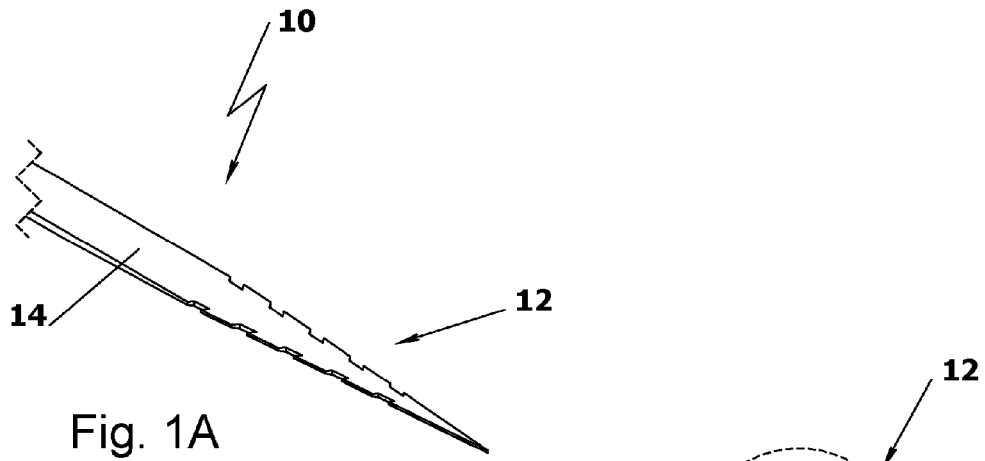
FIGS. 1A-1C are perspective views of an exemplary blade of an embodiment of a tissue sampling device of the present application, FIG. 1C being an enlarged view of area "C" of FIG. 1B.
Figure 1B:
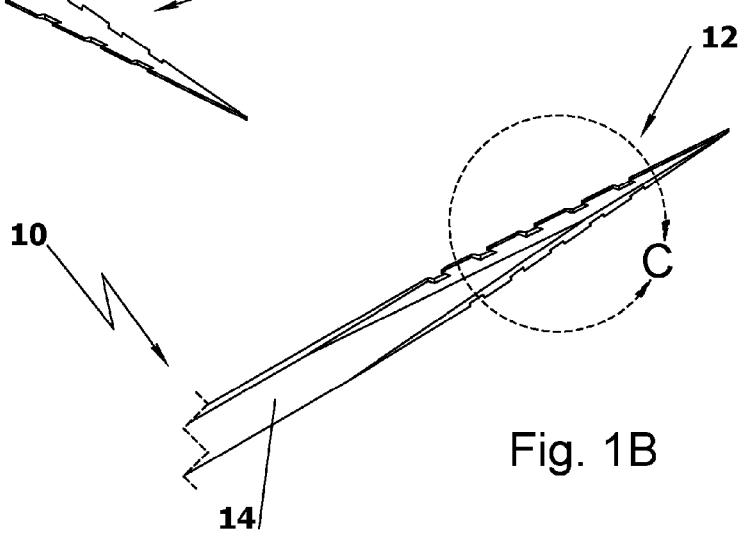
Figure 1C:
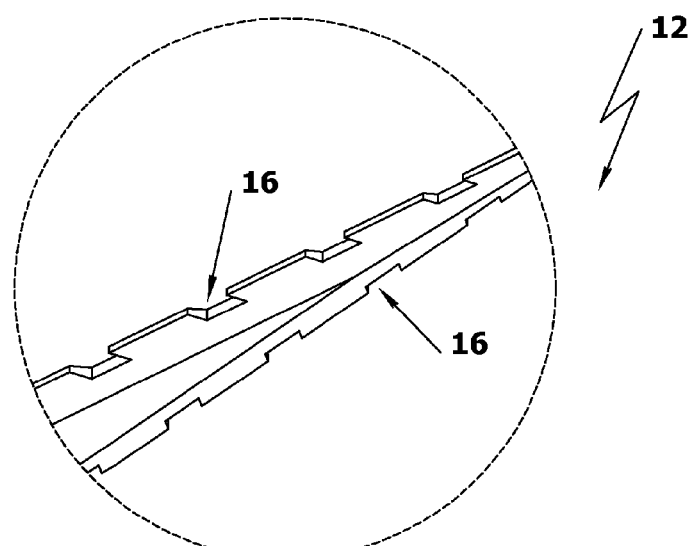

In accordance with some preferred embodiments of the present invention, the device for collecting tissue samples comprises a guide, for example a sheath 20, and a core blade or blade 10. Reference is now made to FIGS. 1A-C, respectively showing perspective bottom, top and enlarged views of anterior portion 12 of blade 10. Blade 10 comprises an elongated and firm, essentially/substantially flat, blade body 14 having an anterior portion 12, having peripheral recesses/notches 16 therein. Anterior portion 12 is typically pointed and adapted to pierce and penetrate into tissue; whereas recesses 16 are adapted to accommodate (receive hold) the collected sample. Recesses 16 typically comprise sharp or pointed edges capable of cutting and ripping-off some of the tissue that anterior portion 12 penetrates into, thereby collecting a sample of the tissue that is captured in recesses 16. It is a particular feature of the device that in some embodiments at least some of the recesses 16 are designed so that the sample collection is accomplished during retraction of the blade 10, rather than insertion of the blade into the tissue.

Reference is now made to FIGS. 1D-1G, showing perspective top views of anterior portions 12A-D, in accordance with some other preferred embodiments of the present invention. Anterior portions 12A-D comprise respective recesses 16A-16D. Recesses 16A-16D vary in shape and location on anterior portions 12A-D; thus adapted for collecting samples from different types of tissues and for different clinical applications.

Figure 2A:
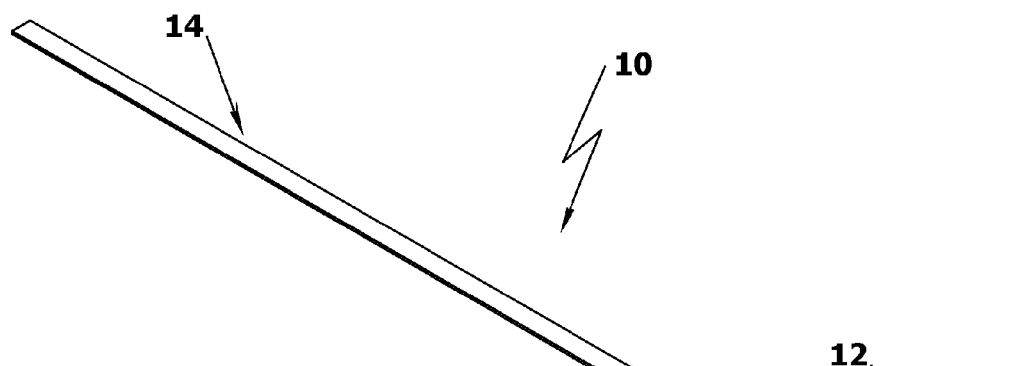
FIGS. 2A-2C are perspective views of an exemplary blade in three bending conformations, a straight, slightly bent and substantially bent conformation, respectively.
Figure 2B:
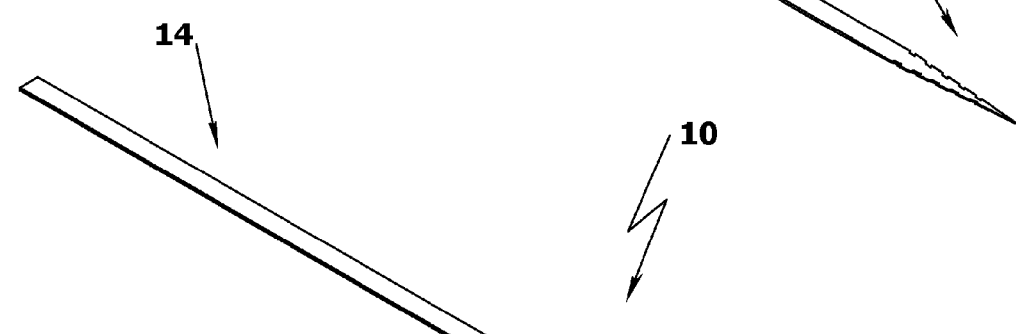

Anterior portion 12 is capable of assuming several conformations. Portion 12 is characterized by a substantial firmness, however by the ability of being bent. Portion 12 thus can assume straight, slightly bent and substantially bent conformations, respectively shown in FIGS. 2A-2C to which reference is now made.

To confer to the portion 12 a bent conformation, blade 10 is inserted into a sheath 20; side, front and cross-sectional views of which are shown in FIGS. 3A-3C to which reference is now made. Sheath 20 comprises a blade guide exemplified by a generally cylindrical elongated sheath body 22, having an interior lumen 23. While the generally cylindrical shape of sheath body 22 is suitable for many if not most applications, in other embodiments the body can have a generally oval, rectangular of other cross section, as suits the use of the device. In its anterior portion 25, sheath body 22 comprises an arcuate slot 26. Arcuate slot 26 forms a continuum between interior lumen 23 and exterior aperture 28, at the end thereof, disposed laterally (i.e. not longitudinally, for example perpendicularly or at another angle non-parallel angle) on sheath body 22.

From the posterior end of sheath body 22, an introducer 24 typically extends. A portion of introducer 24 can be embedded or otherwise connected with cylindrical sheath body 22. Blade 10 (not seen in FIGS. 3A-3C) is inserted into sheath 20 via the posterior end (see FIG. 5A) of the sheath, throughout introducer 24 and further throughout lumen 23, so that anterior portion 12 of the blade is inserted into arcuate slot 26.

Method of Sampling

To collect a sample, the blade 10 is inserted and inwardly advanced within sheath 20, so that the anterior portion 12 of the blade is introduced into arcuate slot 26. Upon such introduction, a bent conformation is conferred to the anterior portion 12 of the blade 10. The blade 10 is forced into and inwardly advanced within sheath 20 until the tip of the anterior end 12 is about to outwardly protrude from arcuate slot 26. Provided that arcuate slot 26 of sheath 20 is positioned adjacent to the tissue where a sample is to be collected, a further advancing of the blade 10 into sheath 20 results in that the anterior portion 12 of the blade outwardly protrudes from arcuate slot 26 and penetrates into the tissue adjacent to arcuate slot 26 of sheath 20. Upon the aforementioned penetration, minute pieces of the tissue and/or clusters of cells are captured within the recesses 16 of the blade 10; and in preferred embodiments, during removal of the blade from the tissue (backward direction).

Subsequently, blade 10 is pulled back relatively to sheath 20, whereby the blade's anterior portion 12 is withdrawn from the tissue and retracted into the sheath body 22 of the sheath. The sheath 20 is then typically removed by pulling on the introducer 24 away of the tissue, while the anterior portion 12 of the blade 10 is shielded by the sheath body 22; thus the samples accommodated within the notches 16 of the blade, which are encompassed within the sheath body 22.

The Benefits of Implementing the Present Device and Method

The present invention is preferably to be used for collecting samples of a tissue bordering a natural anatomic passage, cavity or tubuloalveolar structure formed within a body or an organ, such as the gastrointestinal tract, respiratory tract urinary tract and male or female reproductive tract, including the nose, pharynx, esophagus, stomach, small intestine and particularly duodenum, colon, trachea, pancreas, bronchi, urethra, prostate, ureters, bladder, cervix, vagina, uterus, fallopian tubes, placenta, ovaries and other suitable vascular parts or lumens/vessels. The device of the present invention, nonetheless, can be beneficially used in any clinical application involving endoscopy. It is further emphasized that the device of the present invention can be combined with any endoscope and/or any medical device used for endoscopic procedures.

Figure 4A:
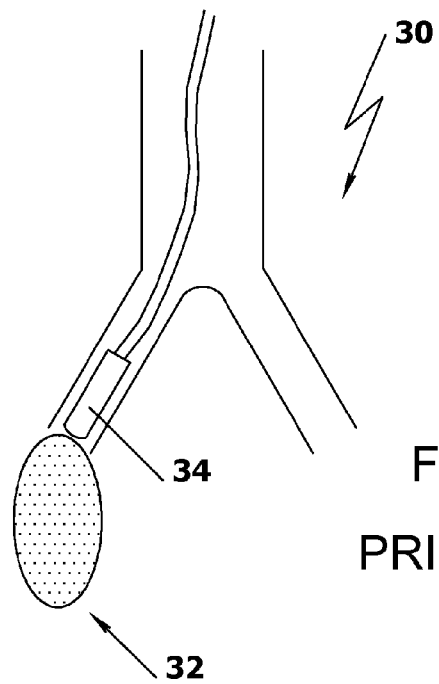
FIGS. 4A-4C are schematic views illustrating operation of a tissue sampling device, FIGS. 4A and 4B depicting prior art sampling operations and FIG. 4C depicting operation of the tissue sampling device of the present application.
Figure 4B:
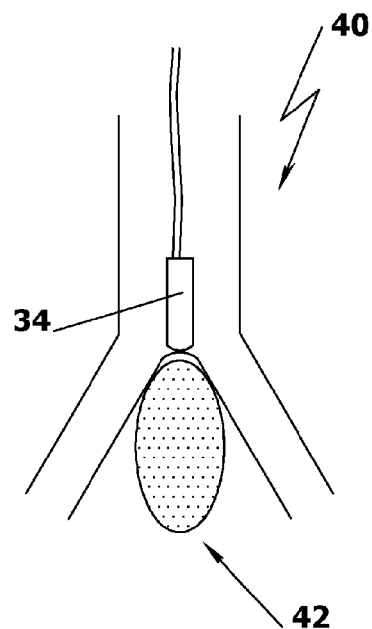
Figure 4C:
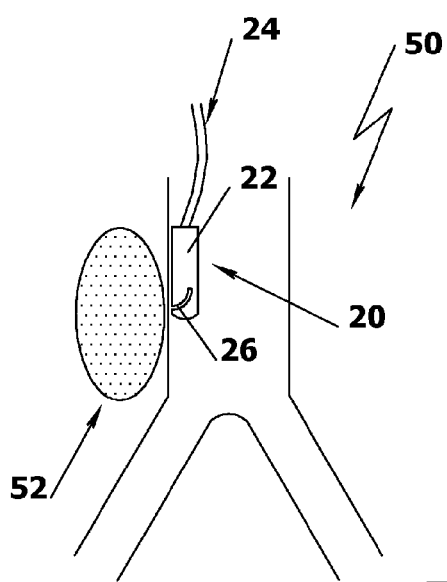

The sheath 20 is introduced into the natural anatomic passage, cavity or tubuloalveolar structure or organ, preferably from an orifice, opening or sphincter at the terminus thereof; thereby providing for a minimally invasive procedure of collecting a tissue sample. To describe the operation of the tissue sample collecting device, reference is now made to FIGS. 4A-4C. Tissue sample collecting devices known in the art are capable of collecting a sample of tissue situated in front of the longitudinal axis thereof, as shown in FIGS. 4A and 4B; whereas the tissue sample collecting device of the invention is characterized by the ability of collecting a sample of tissue located laterally thereto, as shown in FIG. 4C. According to schematic representations of tracts 30 and 40, the location of tissues 32 and 42 therein, wherefrom a sample is to be collected, allows prior art sample collecting devices, such as prior art device 34, to approach tissues 32 and 42 located longitudinally in front of device 34. Prior art device 34 would fail, however, to efficiently collect a sample of tissue 52 located laterally to tract 50; whereas tissue sample collecting device of the invention provides for efficiently collecting a sample of tissue 52 located laterally to tract 50. Sheath 20 of the tissue sample collecting device of the invention is introduced into tract 50, typically by manipulating introducer 24. Body 22 of sheath 20 is thence positioned within tract 50 in such a manner that the exterior aperture within body 22 at the end of arcuate slot 26 faces tissue 52. The positioning of the sheath 20 and/or verification thereof can be performed by any means known in the art, including imaging, endoscopy, triangulation, etc. The blade 10 (not shown in these Figs.) is then operated according to the procedure elaborated supra to collect a sample of tissue 52.

FIGS. 5A and 5B show additional embodiments of the tissue sampling device wherein sheath body 22 has a generally closed configuration, as compared to the embodiment illustrated in FIGS. 3A and 3B wherein the width of arcuate slot 26 is as wide as the sheath body. Thus, anterior portion 12 of blade 10 is only exposed to the surroundings after the blade has been advanced so that the tip of anterior end 12 outwardly protrudes from arcuate slot 26. In FIG. 5A, adjacent the distal end of slot 26, sheath body 22 has a concave hemispherical-shaped portion 60 which can also or alternatively be used to help direct the angle of blade 10 as anterior portion 12 thereof protrudes. In FIG. 5B, the distal end of slot 26 is more in the form of a post box opening.

Without limitation, the present tissue sampling device is particularly suited for retrieving a tissue sample of tissue 52 wherein the tissue is located on the other side of tract 50.

It is a particular feature of the present tissue sampling device that it is designed to result in minimal collateral tissue damage as blade 10 is directed essentially linearly outward from slot 26. Although blade 10 is bendable and returns to its original configuration to allow sample retrieval, due to the curved design of arcuate slot 26, the blade need not be spring loaded to any predetermined configuration (and typically is not). Such spring loading potentially causes collateral tissue damage upon straightening, the straightening resulting in a potentially undesirable sweeping movement of the blade as exemplified in FIG. 12 of WO 2006/015302 (Schomer; X-Sten) and FIGS. 2B and 4C of US 2002/183758 (Middleton). In contrast, due to the design of the present device, blade 10 exits slot 26 in a jabbing or thrusting (straight outward) motion as best understood from and seen in FIG. 5A.

It should be noted that due to the linearly outward directing of blade 10 from slot 26, the penetration force is based on the typically high longitudinal strength/firmness of the blade and therefore may more easily penetrate tissue including relatively hard tissue or even bone. Furthermore, due to the lack of biasing of blade 10, it may be easier to retract the blade after a sample has been obtained.

Figure 2C:
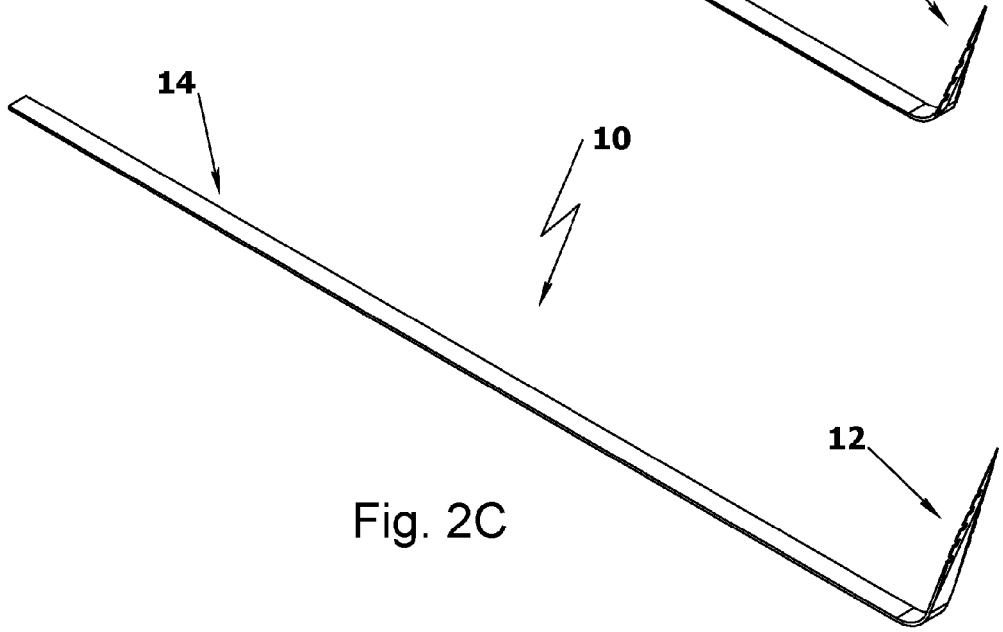

It should be understood that the curvature of arcuate slot 26 is designable to a wide variety of angles, and according to some preferred embodiments, the arcuate slot is configured so that anterior portion 12 of blade 10 extends from sheath body 22 at an angle perpendicular to the sheath body, as understood from FIG. 2C.

Figure 6B:
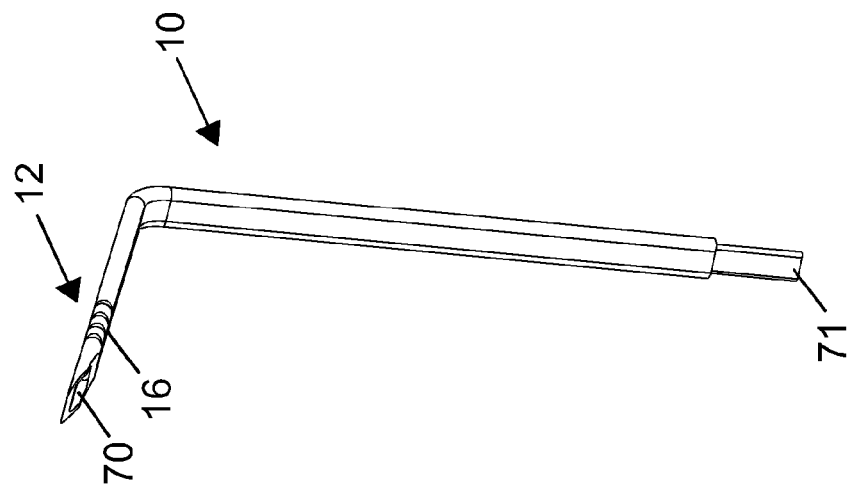
FIGS. 6A and 6B are perspective views of further embodiments of the present tissue sampling device illustrating additional exemplary blade designs.
Figure 6A:
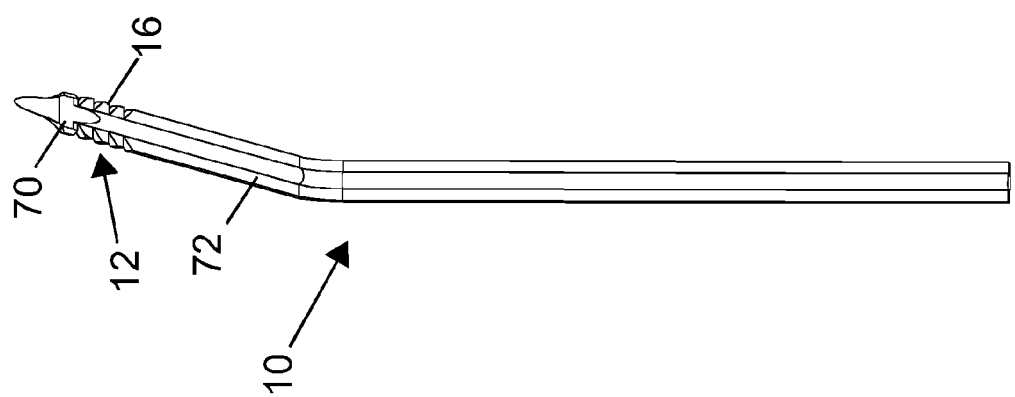

FIGS. 6A and 6B show further exemplary embodiments of the blade 10 wherein the blade comprises a passageway or channel 70 longitudinally disposed in the blade, typically in a central portion thereof, as shown. The channel 70 typically extends from a distal end of the blade 10 to the anterior portion 12 thereof. The channel 70 can allow the removal of material via suction, i.e. be considered a sampling means such as recesses/notches 16; and/or the delivery/injection of material (e.g. a fluid to ease sampling, a medicament, an ink and the like). As such, the blade 10 fulfils the implementation of a needle. The device may in such case include a suction mechanism such as suction needle 71, partially visible.

The embodiment of the blade 10 shown in FIG. 6A further comprises sides or wings 72, typically in at least a section of anterior portion 12. In this embodiment, wings 62 are tapered; and the wings may also comprise recesses/notches 16. Thus, as can be seen, the blade's profile is not rectangular as typical of aforementioned embodiments, rather has a butterfly-like profile. The blade 10 of FIG. 6B has a more rounded profile and less pointy anterior portion 12.

This needle-like aspect of the blade 10 of the latter embodiment can also allow the insertion of another tool through the sheath 20 or sheath body 22 for example an optic fiber or another tool (not shown). Thus, in these embodiments, the blade 10 of the sampling device can comprise both at least one recess or notch 16, adapted to collect a tissue sample, and channel 70, whereby positioning of the device can be achieved "by way of" the blade (e.g. with an optic fiber disposed in the blade; alternatively, disposed in sheath 20/sheath body 20), and the blade can collect a tissue sample.

According to some embodiments, the device comprises an auxiliary channel/conduit (not shown, in the blade 10 or sheath/sheath body 20, 22) for allowing the insertion of the aforementioned other tool, for example an optic fiber, etc. Thus, the device can sample with recesses/notches 16 and/or via channel 70 (or deliver medicament, etc through the channel) and further facilitate use of another tool, such as an optic fiber for illumination at the same time.

The foregoing description is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims.

Further, it should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

The invention claimed is:

1. A device for collecting a tissue sample comprising:
    a blade comprising an elongated blade body terminating anteriorly in a sharp end adapted to pierce and penetrate tissue;
    at least one recess or notch
        defined on said body behind said sharp end,
        said recess or notch being sized to receive and hold said tissue sample,
        said recess or notch comprising a sharp edge positioned to cut away said tissue sample from said penetrated tissue upon withdrawal of said blade therefrom, and
        said tissue sample being removed along with said recess or notch upon said withdrawal; and
    a sheath comprising an elongated sheath body having an interior lumen with an arcuate slot forming a continuum between the interior lumen and an exterior aperture at the end thereof;
    wherein the exterior aperture is disposed laterally on the sheath body and the cross section of the arcuate slot generally corresponds in shape to the longitudinal profile of the blade.

2. The device as in claim 1, adapted whereby the blade is directed essentially linearly outward from the slot.

3. The device as in claim 1, wherein the blade has a substantially flat profile.

4. The device as in claim 1, wherein the blade comprises a channel longitudinally disposed in the blade.

5. The device as in claim 4, wherein the channel is operative for the insertion of an optic fiber therethrough.

6. The device as in claim 4, wherein the channel is operative for the injection of a material therethrough.

7. The device as in claim 1, further comprising an auxiliary conduit in either or both the blade or the sheath.

8. The device as in claim 1, wherein the sheath further comprises an introducer used for positioning of the sheath body.

9. The device as in claim 1, wherein the blade is inserted into the sheath, at least partially within said slot.

10. The device as in claim 1, wherein the sheath further comprises a channel for facilitating the presence of an additional tool in the area of the tissue.

11. A device according to claim 1, wherein said at least one recess or notch comprises a plurality of non-interconnecting recesses or notches, each of said recesses or notched adapted to receive and hold a tissue sample.

12. A device according to claim 1, wherein said at least one recess or notch is positioned on the edges of the blade body.

13. A device according to claim 1, wherein said at least one recess or notch comprises a recess or hole in the blade body.

14. A method of collecting tissue samples, comprising:
    piercing body tissue with a sharp anteriorly-disposed tip of a flat blade;
    penetrating—with the body of said blade following said anteriorly-disposed tip—into said tissue, to insert a recess or notch region located along said blade into said body tissue, said penetrating comprising bending an anterior portion of the blade;
    retracting said blade together with said recess or notch from said body tissue, thereby cutting said body tissue with an edge of said recess or notch region,
    capturing at least a portion of said cut body tissue within said recess or notch, and
    extracting said portion of said cut body tissue as a tissue sample held by said recess or notch.

15. The method of claim 14, comprising:
    positioning a side aperture of a sheath body to face said body tissue; wherein
    said piercing comprises said flat blade issuing from said side aperture.

16. The method according to claim 15, further including inserting an optic fiber in a channel of the blade or of the sheath body for providing illumination.

17. A method according to claim 14, wherein said penetrating comprises penetrating with a substantially flat portion of the blade.

* * * * *